United States Patent [19]

King, Jr. et al.

[11] Patent Number: 5,399,734
[45] Date of Patent: Mar. 21, 1995

[54] METHOD FOR MAKING AROMATIC ORGANIC CARBONATES

[75] Inventors: Joseph A. King, Jr., Schenectady; Patricia D. Mackenzie, Clifton Park; Eric J. Pressman, East Greenbush, all of N.Y.

[73] Assignee: General Electric Company, Schenectady, N.Y.

[21] Appl. No.: 93,918

[22] Filed: Jul. 20, 1993

Related U.S. Application Data

[63] Continuation of Ser. No. 906,681, Jul. 7, 1992, abandoned, which is a continuation-in-part of Ser. No. 737,109, Jul. 29, 1991, abandoned.

[51] Int. Cl.$^6$ .............................................. C07C 69/96
[52] U.S. Cl. .................................... 558/270; 558/271; 558/274
[58] Field of Search ................................ 558/274, 270

[56] References Cited

U.S. PATENT DOCUMENTS 4,361,519  11/1982  Hallgren .............................. 558/270

FOREIGN PATENT DOCUMENTS 350700  6/1989  France .

Primary Examiner—José G. Dees
Assistant Examiner—Dwayne C. Jones
Attorney, Agent, or Firm—William A. Teoli; William H. Pittman

[57] ABSTRACT

Improved yields of aromatic organic carbonates made by the palladium catalyzed direct carbonylation of aromatic organic hydroxy compounds can be achieved if the total gas pressure and partial pressure of carbon monoxide and oxygen are substantially maintained during the reaction.

6 Claims, 1 Drawing Sheet

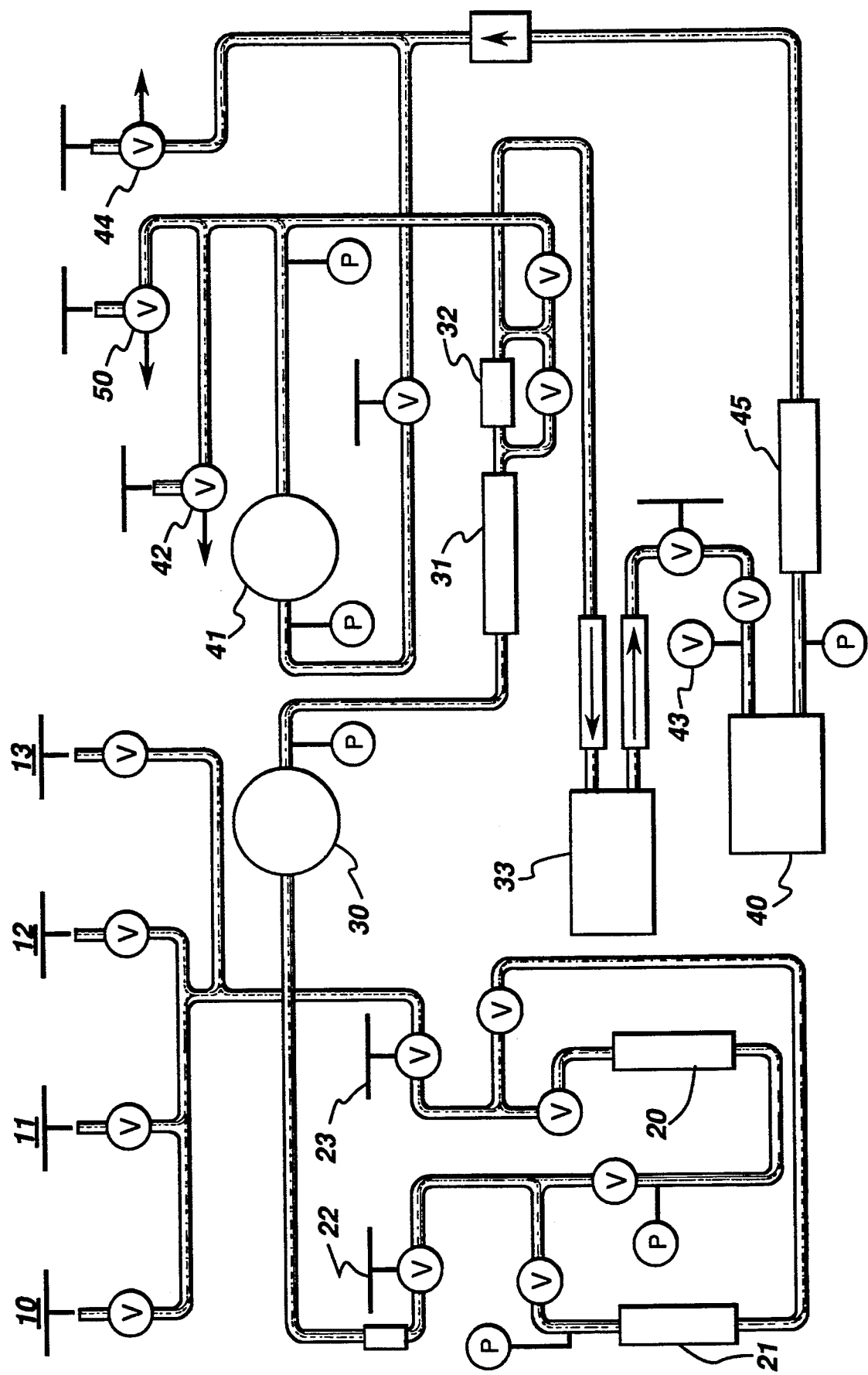

5,399,734

METHOD FOR MAKING AROMATIC ORGANIC CARBONATES

This application is a continuation of application Ser. No. 07/906,681, filed Jul. 7, 1992, now abandoned, which is a continuation-in-part of application Ser. No. 07/737,109, filed Jul. 29, 1991, now abandoned.

BACKGROUND OF THE INVENTION

The present invention relates to a method for making aromatic organic carbonates such as diphenyl carbonate by effecting reaction between an aromatic organic hydroxy compound, such as phenol, and carbon monoxide and oxygen in the presence of an effective amount of a palladium carbonylation catalyst. More particularly, the present invention relates to the carbonylation of an aromatic organic hydroxy compound such as phenol utilizing a mixture of carbon monoxide and oxygen under constant flow conditions to maintain the carbon monoxide and oxygen at a substantially constant molar ratio and partial pressure during the course of the reaction.

Procedures for making diorganic carbonates are shown by Hallgren, U.S. Pat. Nos. 4,361,519 and 4,410,464, utilizing a molecular sieve as a drying agent for the water formed during the reaction and Japanese patent 01,165,551. Aromatic organic carbonates are of particular interest to thermoplastic manufacturers, since they offer an alternative nonphosgene route to aromatic polycarbonates by melt transesterification. A procedure for making aromatic organic carbonates using an organic solvent, such as methylene chloride, is shown by Chalk, U.S. Pat. No. 4,187,242. Reference also is made to T. C. Chang in copending application Ser. No. 217,248, filed Jul. 11, 1988 now abandoned, and EP350-700-A, utilizing a divalent or trivalent manganese salt or cobalt (II) salt and hydroquinone in combination with a palladium catalyst, to catalyze the conversion of an aromatic organic hydroxy compound, such as phenol, to an aromatic organic carbonate. U.S. Pat. No. 4,218,391,Romano et al employ a copper salt to prepare organic esters of carbonic acid. Attempts to use such catalyst with aromatic organic hydroxy compounds, such as phenol, under constant flow conditions have been found to provide unsatisfactory results with respect to % carbonate yields and % carbonate selectivity as compared to the use of aliphatic hydroxy compounds, such as methanol, in preparing aliphatic carbonates under substantially the same conditions.

Aromatic organic carbonates such as diphenyl carbonate made by effecting reaction at elevated pressures in a reactor between components such as, phenol, carbon monoxide, an oxidant and a Group VIII catalyst are generally limited to batch conditions, whereby the pressures of the reacting gases, such as carbon monoxide and oxygen decrease with time and their relative reaction ratio change. Efforts to introduce into the reactor, make-up carbon monoxide and oxygen to improve aromatic organic hydroxy compound conversion, by shutting down the reactor have been unsuccessful because the activity of the Group VIII catalyst is often adversely affected if it is exposed to ambient conditions for even a relatively short period of time.

As a result additional methods are constantly being evaluated to achieve higher reaction rates and aromatic carbonate yields, as well as permitting quantification of reaction rate with respect to gas partial pressure.

SUMMARY OF THE INVENTION

The present invention is based on the discovery that in the synthesis of aromatic organic carbonate by the direct carbonylation of an aromatic organic hydroxy compound, such as phenol, with carbon monoxide and oxygen in the presence of a palladium catalyst, improved reaction rates and yields of an aromatic organic carbonate can be achieved by continuously introducing makeup carbon monoxide and oxygen into a reactor in amounts to substantially maintain their partial pressures and reactant ratios during the course of the carbonylation reaction.

STATEMENT OF THE INVENTION

There is provided by the present invention, a method for making an aromatic organic carbonate which comprises, (1) charging a reactor with an aromatic organic hydroxy compound and an amount of a palladium catalyst which is sufficient to catalyze the carbonylation of the aromatic organic hydroxy compound, (2) introducing into the reactor, a mixture of oxygen and carbon monoxide until a pressure of 200 psi to 3500 psi at 25° C. is achieved, where the oxygen and carbon monoxide mixture contains 2 to 50 mole % of oxygen based on the total moles of carbon monoxide and oxygen, (3) agitating and heating the resulting mixture to a temperature of 40° C. to 175° C., while maintaining the total reaction pressure and the partial pressures of carbon monoxide and oxygen in the mixture substantially constant until the aromatic organic hydroxy compound is substantially converted to aromatic organic carbonate, (4) recovering aromatic organic carbonate from the mixture of (3).

Aromatic organic hydroxy compounds which can be used in the practice of the invention include aromatic mono or polyhydroxy compounds, such as phenol, cresol, xylenol, resorcinol, hydroquinone, and bisphenol A. Aromatic organic mono hydroxy compounds are particularly preferred, with phenol being the most preferred.

The palladium material useful as a catalyst can be in elemental form, or it can be employed as a palladium compound. Accordingly, palladium black or elemental palladium deposited on carbon can be used as well as palladium compounds, such as halides, nitrates, carboxylates, oxides and complexes involving such compounds such as carbon monoxide, amines, phosphines or olefins. The preferred palladium compounds are palladium (II) salts of organic acids including carboxylates with $C_{2-6}$ aliphatic acids. Palladium (II) acetate is particularly preferred. There also can be used in combination with palladium catalyst, tetraalkylammonium halide or tetraalkylphosphonium halide, such as the chlorides and bromides and particularly the bromides. Alkyl groups of the alkyl ammonium halides are primary and secondary alkyl groups containing about 1–8 carbon atoms. Tetra-n-butylammonium bromide is particularly preferred. There also can be used in combination with the palladium catalyst and the tetraalkylammonium halide at least one quinone and aromatic diol formed by the reduction of said quinone or a mixture of thereof. 1,4-benzoquinone and hydroquinone are preferred. In addition, compounds such as 1,2-quinone and catechol, anthraquinone, 9,10-dihydroxyanthracene, and phenanthrenequinone also can be used.

In instances where the formation of aromatic organic carbonates, such as diphenyl carbonate, is desired, manganese or cobalt cocatalysts also can be used. For example, cobalt or manganese compounds such as divalent or trivalent compounds, for example, salts such as halides and carboxylates and complexes with amines, diketones and carbon monoxide have been found effective. Cobalt (II) acetate is particularly preferred. It has been found that optimum selectivity i e., optimizing the formation of aromatic carbonate and minimizing the formation of aromatic salicylate is achieved using the cobalt (II) catalyst.

An effective amount of the palladium catalyst is, for example, an amount sufficient to provide about 1 gram-atom of palladium, per 800–10,000 and preferably 5,000–10,000 moles of aromatic organic hydroxy compound. The other components of the palladium catalyst are, for example, per gram-atom of palladium, about 0.1–5.0, preferably about 0.5–1.5 gram-atoms of manganese or cobalt and about 5 to 150 and preferably about 20–50 moles of the tetraalkylammonium halide and about 10–60 and preferably about 25–40 moles of quinone and/or reduction product thereof.

Solid drying agents,, such as molecular sieves, can be used to improve: yields. In some instances, carbon dioxide also can be used as a dessicant as taught in copending application Ser. No.07/503,404, filed Apr. 2, 1990 now abandoned.

BRIEF DESCRIPTION OF THE DRAWING

In order that those skilled in the art will be better able to practice the present invention reference is made to the drawing. The drawing shows a schematic of a gas flow reactor system for preparing aromatic organic carbonate capable of delivering in a continuous manner at a flow rate about 50 ml to 1000 ml and preferably ,about 300 ml to 600 ml per min, a mixture of carbon monoxide and oxygen maintained at a substantially constant molar ratio and partial pressures. In the schematic, "V" indicates a manual value and "P" indicates a pressure gauge.

More particularly, there is shown at 10 a carbon monoxide gas inlet and at 11, an oxygen inlet. 12 is a manifold vent, and 13 is an optional inlet for a gas, such as carbon dioxide.. The reaction mixture can be fed into a low pressure reservoir at 20, or a high pressure reservoir at 21 which can be operated at a higher pressure than the reactor for the duration of the run. At 22 there is shown a reservoir outlet and at 23 a reservoir inlet. The gas feed pressure can be adjusted to about 50 psi over the desired reactor pressure at a reducing pressure regulator at 30. The gas can be further purified in scrubber 31 and then fed into a mass flow controller at 32 to allow for the previously described flow rates. The reactor feed gas can be heated in an oil bath at 33 having appropriate conduit means prior to being introduced to the reactor at 40. The reactor pressure can be controlled through manipulation of a back pressure regulator at 41. The reactor gas effluent may be either sampled for further analysis at 42 or vented to the atmosphere at 50. The reactor liquid can be sampled at 43. 45 is a condenser. An additional vent at 44 can allow for further system control, but is typically closed during the gas flow reaction.

In the practice of one form of the invention, the palladium catalyst, co-catalyst package, and aromatic organic hydroxy compound are charged to the reactor. The reactor is sealed. Carbon monoxide and oxygen are introduced into an appropriate reservoir within proportions previously defined, until a suitable pressure such as 2800 psi is achieved.

Circulation of condenser water is initiated and the oil bath temperature can be raised to 100° C. Conduit between the oil bath and the reactor can be heated using heat tape to a suitable temperature such as 100° C. The mass flow bypass can be opened and an appropriate accumulator valve can be opened and the reducing pressure regulator can be used to adjust the pressure. The reactor pressure can be further adjusted by the back pressure regulator. The mass flow bypass can be closed and the flow can be adjusted using the mass flow controller. Agitation of the reaction ingredients can be initiated once the reactor temperature is raised sufficiently to minimize the presence of solids such as phenol. Upon reaching a desirable reactor temperature, such as 100° C., aliquots can be taken to monitor the reaction.

In order that those skilled in the art will be better able to practice the present invention, the following examples are given by way of illustration and not by way of :limitation. All parts are by weight unless otherwise indicated.

EXAMPLE 1

There was added to a tantalum lined flow reactor at room temperature, 59.385 g (631 mmol) of phenol, 1.015 g (3.15 mmol) of tetrabutylammonium bromide, 0.014 g (0.079 mmol) of cobalt diacetate, 0.171 g (1.58 mmol) of benzoquinone and 0.018 g (0.080 mmol) of palladium diacetate providing 141 ppm of palladium. The reactor vessel was sealed. The reservoir was then charged with 200 psi of oxygen and 2600 psi of carbon monoxide (7.1% of $O_2$ in CO) providing a total pressure (Pt) of 2800 psi. The mixture of the reservoir was continuously introduced into the reaction mixture at a rate of about 350 ml/min.

The reactor was heated to 100° C. over a period of 15 minutes. Stirring at 540–550 rpm was initiated once the reactor temperature reached 40° C. Aliquots were taken periodically for GC analysis once the reaction temperature reached 100° C. At 0.0 hours, the yield of diphenyl carbonate was 0.021 g (0.03%). Subsequent yields were found to be 3.83 g (5.66%) at 2 hours, 6.08 g (9.00%) at 5 hours, 7.22 g (10.5%) at 6 hours, 8.14 g (12.1%) at 7 hours, and a yield of 8.72 g (12.9%) at the end of 11 hours.

EXAMPLE 2

The procedure of example 1 was repeated, except that there was utilized 60.639 g (644 mmol) of phenol, 4.089 g (12.3 mmol) of tetrabutylammonium bromide, 0.0638 g (0.360 mmol) of cobalt diacetate, 0.6954 g (6.43 mmol) of benzoquinone and 0.0738 g (0.329 mmol) of palladium diacetate to provide 534 ppm of palladium. After 0.0 hours, the yield of diphenyl carbonate was 0.2 g (0.3%). After 0.5 hours, the yield of diphenyl carbonate was 1.69 g (2.4%). Additional aliquots were taken at 1 hour to provide yields of 3.81 g (5.5%), at 2 hours to provide 6.86 g (9.9%), at 3.5 hours to provide; 9.47 g (13.7%), at 5 hours there was obtained 11.52 g (16.7%), and at 6 hours, 12.17 g (17.6%). At the termination of the reaction, (7.0 hours) there was obtained a yield of 15.72 g (22.8%) of diphenyl carbonate.

EXAMPLE 3

The procedure of example 1 was substantially repeated except that there was utilized in the mixture 23.37 g of 4Å molecular sieves which were activated after heating at 300° C. for 12 hours. Upon reaching a reactor temperature of 100° C., aliquots taken periodically for GC analysis showed diphenyl carbonate yields after 0.0 hour of 0.257 g (0.39%), 2 hours of 4.99 g (7.33%), and 5 hours of 7.97 g (11.71%). Subsequent diphenyl carbonate yields were found after 7 hours to be 10.50 g (15.41%), at 8 hours 11.97 g (17.56%) and at 9 hours, 12.62 g (18.52%). The reaction was continued, and at 10 hours 13.37 g (19.62%), and 11 hours there was obtained 14.46 g (21.24%). At the end of a 15 hour reaction period, a yield of 15.15 g (22.23%) Of diphenyl carbonate was obtained.

EXAMPLE 4

The procedure of example 1 was repeated, except that 23.71 g of 4Å molecular sieves were used which had been activated by heating at 300° C. for about 12 hours. There was employed 59.336 g (630 mmol) of phenol, 3.048 g (7.99 mmol) of tetrabutylammonium bromide, 0.0270 g (0.0763 mmol) of cobalt diacetate, 0.345 g (1.596 mmol) of benzoquinone and 0.0370 g (0.0824 mmol) of palladium diacetate, which provided 284 ppm of palladium.

At a reactor temperature of a 100° C., aliquots for GC analysis showed that after 0.0 hour, there was obtained a diphenyl carbonate yield of 0.386 g (0.58%). Yields taken between the period of from 2 hours to 12 hours showed the following:

| Reaction Time (hr) | Diphenyl Carbonate Yield (%) |
|---|---|
| 2 | 13.02 |
| 5 | 17.56 |
| 7 | 25.75 |
| 8 | 28.51 |
| 9 | 29.37 |
| 10 | 30.15 |
| 11 | 31.48 |
| 12 | 29.60 |
| 13 | 30.62 |

EXAMPLE 5

The procedure of example 3 was repeated utilizing 24.42 g of 4Å molecular sieves as a desiccant. In addition, there was utilized 59.045 g (6.27 mmol) of phenol, 4.097 g (12.7 mmol) of tetrabutylammonium bromide, 0.0640 g (0.362 mmol) of cobalt diacetate, 0.6960 g (6.44 mmol) of benzoquinone, and 0.0730 g (0..325 mmol) of palladium diacetate sufficient to provide 541 ppm of palladium.

When reactor temperature of 100° C. was achieved aliquots were taken periodically for GC analysis to determine diphenyl carbonate yield. The following results were obtained over a period of from 0 to 12 hours:

| Reaction Time (hr) | Diphenyl Carbonate Yield (%) |
|---|---|
| 0 | 1.44 |
| 2 | 12.72 |
| 5 | 21.54 |
| 7 | 32.22 |
| 8 | 37.20 |
| 9 | 37.16 |
| 10 | 39.09 |
| 11 | 43.06 |
| 12 | 40.57 |

Although the above examples are directed to only a few of the very many variables which can be employed in the practice of the method of the present invention, it should be understood that the present invention is directed to the use of a much broader variety of catalysts, reactants, and conditions as set forth in the description preceding the examples.

What is claimed is:

1. A method for making an aromatic organic carbonate which comprises,
   (1) agitating and heating in a reactor to a temperature of between 40° C. to 175° C., a mixture comprising an aromatic organic hydroxy compound, oxygen and carbon monoxide and an amount of a palladium catalyst which is sufficient to catalyze the carbonylation of the aromatic organic hydroxy compound, where during the carbonylation of the aromatic hydroxy compound, the mixture of carbon monoxide and oxygen is maintained in the reactor at a substantially constant molar ratio and partial pressure to provide the substantial conversion of the aromatic organic hydroxy compound to aromatic organic carbonate without interruption as a result of the use of a gas flow reactor system comprising, the reactor, a carbon monoxide gas inlet, an oxygen gas inlet, a reservoir for storing a mixture of carbon monoxide and oxygen having inlet and outlet means, a pressure reducing regulator, a mass flow controller, and a back pressure regulator, and
   (2) recovering the aromatic organic carbonate from the resulting mixture of (1).

2. A method in accordance with claim 1, where the aromatic organic hydroxy compound is phenol.

3. A method in accordance with claim 1, which utilizes a desiccant.

4. A method in accordance with claim 3, where the desiccant is a molecular sieve.

5. A method in accordance with claim 1, where the palladium catalyst is palladium diacetate.

6. A method in accordance with claim 1, where the palladium catalyst is used in combination with tetrabutylammonium bromide, cobalt diacetate and benzoquinone.

* * * * *